(12) United States Patent
Rigby

(10) Patent No.: US 9,375,197 B2
(45) Date of Patent: Jun. 28, 2016

(54) SYSTEMS AND METHODS FOR INVERTED BEAMFORMING

(71) Applicant: General Electric Company, Schenectady, NY (US)

(72) Inventor: Kenneth Wayne Rigby, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 274 days.

(21) Appl. No.: 13/743,136

(22) Filed: Jan. 16, 2013

(65) Prior Publication Data

US 2014/0200455 A1    Jul. 17, 2014

(51) Int. Cl.
*A61B 8/00* (2006.01)
*A61B 8/08* (2006.01)
*G01S 7/52* (2006.01)
*G10K 11/34* (2006.01)
(Continued)

(52) U.S. Cl.
CPC .............. *A61B 8/4272* (2013.01); *A61B 8/5207* (2013.01); *G01S 7/52034* (2013.01); *G10K 11/346* (2013.01); *A61B 8/145* (2013.01); *A61B 8/429* (2013.01); *A61B 8/4488* (2013.01); *A61B 8/461* (2013.01); *A61B 8/467* (2013.01); *A61B 8/54* (2013.01); *A61B 8/565* (2013.01); *G01S 15/8915* (2013.01)

(58) Field of Classification Search
CPC .... A61B 8/4272; A61B 8/5207; A61B 8/429; A61B 8/145; A61B 8/461; A61B 8/565; A61B 8/4488; A61B 8/54; A61B 8/467; G10K 11/346; G01S 7/52034; G01S 15/8915

USPC .......................................................... 600/447
See application file for complete search history.

(56) References Cited

U.S. PATENT DOCUMENTS 5,197,037 A * 3/1993 Leavitt ............................ 367/11
5,844,139 A 12/1998 Miller et al.
6,052,427 A 4/2000 Pan
(Continued)

FOREIGN PATENT DOCUMENTS

CN       1714752 A    1/2006
CN     101571518 A   11/2009
(Continued)

OTHER PUBLICATIONS

Karaman et al., "Digital Beamforming Using Non-Uniform Oversampling Delta-Sigma Conversion", 1999 IEEE Ultrasonics Symposium, pp. 1279-1282, 1999.*

(Continued)

*Primary Examiner* — Jonathan Cwern
(74) *Attorney, Agent, or Firm* — Seema S. Katragadda

(57) ABSTRACT

Systems and methods for time-delay inverted beamforming are provided. One method includes sampling, substantially uniformly in time, a set of continuous-time element signals to form a set of sampled element signals and mapping, for each sampled element signal, one or more samples substantially equally spaced in time to one or more samples non-equally spaced in time corresponding to the respective contribution of each element signal to a continuous-time beamsum signal. The method also includes forming a beamsum signal sampled substantially uniformly in time from the non-uniformly spaced, mapped samples corresponding to each sampled element signal.

20 Claims, 6 Drawing Sheets

(51) Int. Cl.
*A61B 8/14* (2006.01)
*G01S 15/89* (2006.01)

(56) References Cited

U.S. PATENT DOCUMENTS

| | | | |
|---|---|---|---|
| 6,747,584 | B2 | 6/2004 | Havelock |
| 7,737,892 | B2 | 6/2010 | Richardson et al. |
| 7,740,583 | B2 | 6/2010 | Rigby et al. |
| 8,241,216 | B2 | 8/2012 | Loftman et al. |
| 8,241,217 | B2 | 8/2012 | Chiang et al. |
| 2005/0228284 | A1* | 10/2005 | Baumgartner et al. ....... 600/459 |

FOREIGN PATENT DOCUMENTS

| | | |
|---|---|---|
| EP | 0539700 A1 | 5/1993 |
| EP | 1808122 A2 | 7/2007 |

OTHER PUBLICATIONS

Jieming Ma et al.: "Software-based Ultrasound Phase Rotation Beamforming on Multi-core DSP"; 5 pgs.

Sohn et al., "Software Implementation of Ultrasound Beamforming using ADSP-TS201 DSPs", Proceedings of SPIE, Volume No. 6920, pp. 1-11, Mar. 13, 2008.

Doblinger., "Beamforming with Optimized Interpolated Microphone Arrays", Hands-Free Speech Communication and Microphone Arrays, pp. 33-36, May 6-8, 2008.

Kozak, "Digital Phased Array Beamforming Using Single-Bit Delta-Sigma Conversion with Non-Uniform Oversampling", IEEE Transactions on Ultrasonics, Ferroelectrics, and Frequency Control, Volume No. 48, Issue No. 4, pp. 922-931,Jul. 2001.

Unofficial English Translation of Chinese Office Action issued in connection with corresponding CN Application No. 201410019458.1 on Jun. 24, 2015.

* cited by examiner

SYSTEMS AND METHODS FOR INVERTED BEAMFORMING

BACKGROUND

The subject matter disclosed herein relates generally to imaging systems and methods and, more particularly, to systems and methods for performing inverted beamforming in ultrasonic imaging systems.

Medical diagnostic ultrasound is an imaging modality that employs ultrasound waves to probe the acoustic properties of the body of a patient and produce a corresponding image. Generation of sound wave pulses and detection of returning echoes is typically accomplished via a plurality of transducers located in the probe. Such transducers typically include electromechanical elements capable of converting electrical energy into mechanical energy for transmission and mechanical energy back into electrical energy for receiving purposes. Some ultrasound probes include up to thousands of transducers arranged as linear arrays or a two-dimensional matrix of elements.

A beamformer is typically associated with the ultrasound probe to combine the signals from each transducer element so as to enhance the response to received acoustic energy from a desired focus depth and direction. In certain ultrasound systems, both the inputs and output of the beamformer, the element signals, and the beamsum signal, are sampled uniformly in time. In certain systems, the beamformer focus function is implemented by calculating for each beamsum sample a corresponding time in each element signal that accounts for the propagation time for acoustic energy emitted from the transducer, reflected from scatterers at the desired focus point and returning to that element. In general, this propagation time used in the focus function will not correspond to one of uniformly spaced element samples that are available. In some traditional beamformers, the value at the focus time is obtained by interpolating the available uniformly spaced element samples to approximate the value that would have been obtained had the element signal been sampled at the focus time.

This interpolation can be performed in dedicated hardware, such as a custom application-specific integrated circuit (ASIC), or in a computer processor, such as a general purpose processor (CPU, or central processing unit) or a graphical processing unit (GPU). The first implementation may be called a hardware beamformer, and the second implementation may be called a software beamformer.

In some applications, it is useful to calculate more than one beamsum signal from the same set of element signals, i.e., from the data acquired during a single transmit event. This increases the maximum image display rate by reducing the number of transmit firings required to form an image over a desired two-dimensional scan area or three-dimensional volume. In a hardware beamformer, the element signal samples are typically processed sequentially as they are produced and then discarded. Forming multiple beamsums typically requires duplicating the interpolation hardware for each beamsum. This tends to be costly in terms of both power and expense, especially in volumetric imaging when many (e.g., approximately 16-64) receive beams are desired for each transmit event.

In a software beamformer, the element signal samples for one or more transmit firings are typically stored in memory temporarily, and the interpolation software accesses the required samples from the memory. In a software beamformer, the number of receive beams that can be calculated is limited primarily by the speed at which the processor can perform the calculations. In many applications, the software beamformer has significant advantages in power consumption and expense compared with the hardware beamformer.

The calculation speed is determined by both the raw speed of the processor, i.e., the rate at which math operations can be performed in the processor, and by the memory bandwidth, the rate at which data can be read and written to memory from the processor. The memory bandwidth may be the limiting factor in applications, such as software beamforming, in which only a small number of math operations needs to be performed on each of a very large number of samples. This is especially true when the memory in a specific application cannot be addressed sequentially, since the interface between processor and memory is typically highly optimized for sequential memory access. Unfortunately, conventional approaches to calculating multiple beamsums in a software beamformer require repeated, non-sequential access to data stored in memory, thus limiting the system efficiency.

BRIEF DESCRIPTION

In one embodiment, a method includes sampling, substantially uniformly in time, a set of continuous-time element signals to form a set of sampled element signals and mapping, for each sampled element signal, one or more samples substantially equally spaced in time to one or more samples non-equally spaced in time corresponding to the respective contribution of each element signal to a continuous-time beamsum signal. The method also includes forming a beamsum signal sampled substantially uniformly in time from the non-uniformly spaced, mapped samples corresponding to each sampled element signal.

In another embodiment, an ultrasound system includes a transducer array having one or more transducers, a transmitter adapted to transmit electrical signals to the transducer array, a receiver adapted to receive electrical signals generated by the transducer array when the one or more transducers detect an ultrasonic echo, transmitter/receiver switching circuitry coupled to the transducer array and adapted to switch the transmitter and the receiver, and an analog-to-digital converter adapted to receive analog data from the receiver corresponding to the ultrasonic echo and to convert the analog data to a digital element signal. The system also includes a beamformer adapted to receive and process the digital element signal to form a beamsum signal. The beamformer is adapted to sample, substantially uniformly in time, a set of continuous-time element signals to form a set of sampled element signals, to map, for each sampled element signal, one or more samples substantially equally spaced in time to one or more samples non-equally spaced in time corresponding to the respective contribution of each element signal to a continuous-time beamsum signal, and to form a beamsum signal sampled substantially uniformly in time from the non-uniformly spaced, mapped samples corresponding to each sampled element signal.

In another embodiment, a computer-readable medium encoding one or more executable routines, which, when executed by a processor, cause the processor to perform acts that include sampling, substantially uniformly in time, a set of continuous-time element signals to form a set of sampled element signals, mapping, for each sampled element signal, one or more samples substantially equally spaced in time to one or more samples non-equally spaced in time corresponding to the respective contribution of each element signal to a continuous-time beamsum signal, and forming a beamsum signal sampled substantially uniformly in time from the non-uniformly spaced, mapped samples corresponding to each sampled element signal.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The time-delay function in beamforming is typically described and implemented as a mapping from uniformly spaced output sample times in the beamsum signal to non-uniformly spaced sample times in the element signals. Since the input samples that are available are uniformly spaced in time, the desired input values are obtained by interpolation. However, as described in more detail below, provided herein are systems and methods directed toward a novel approach to beamforming that inverts this mapping. More specifically, in the provided embodiments, the time-delay function is rewritten to map the uniformly spaced input sample times, which are available in the element signals, to non-uniformly spaced output sample times in the beamsum signal. In provided embodiments, the desired uniformly spaced output sample values are obtained by interpolation from a non-uniform to a uniform sampling time grid. In presently disclosed embodiments of this "inverted beamforming" method, it is only necessary to access each element sample once, regardless of the number of beamsum signals that are calculated from a given set of element samples. The foregoing feature may be advantageous, for example, in software beamforming, particularly when large numbers of beamsum signals are calculated using the same set of element samples, where the memory bandwidth may be a limiting factor. These and other features of the presently disclosed inverted beamforming methods and systems are described in more detail below.

Figure 1:
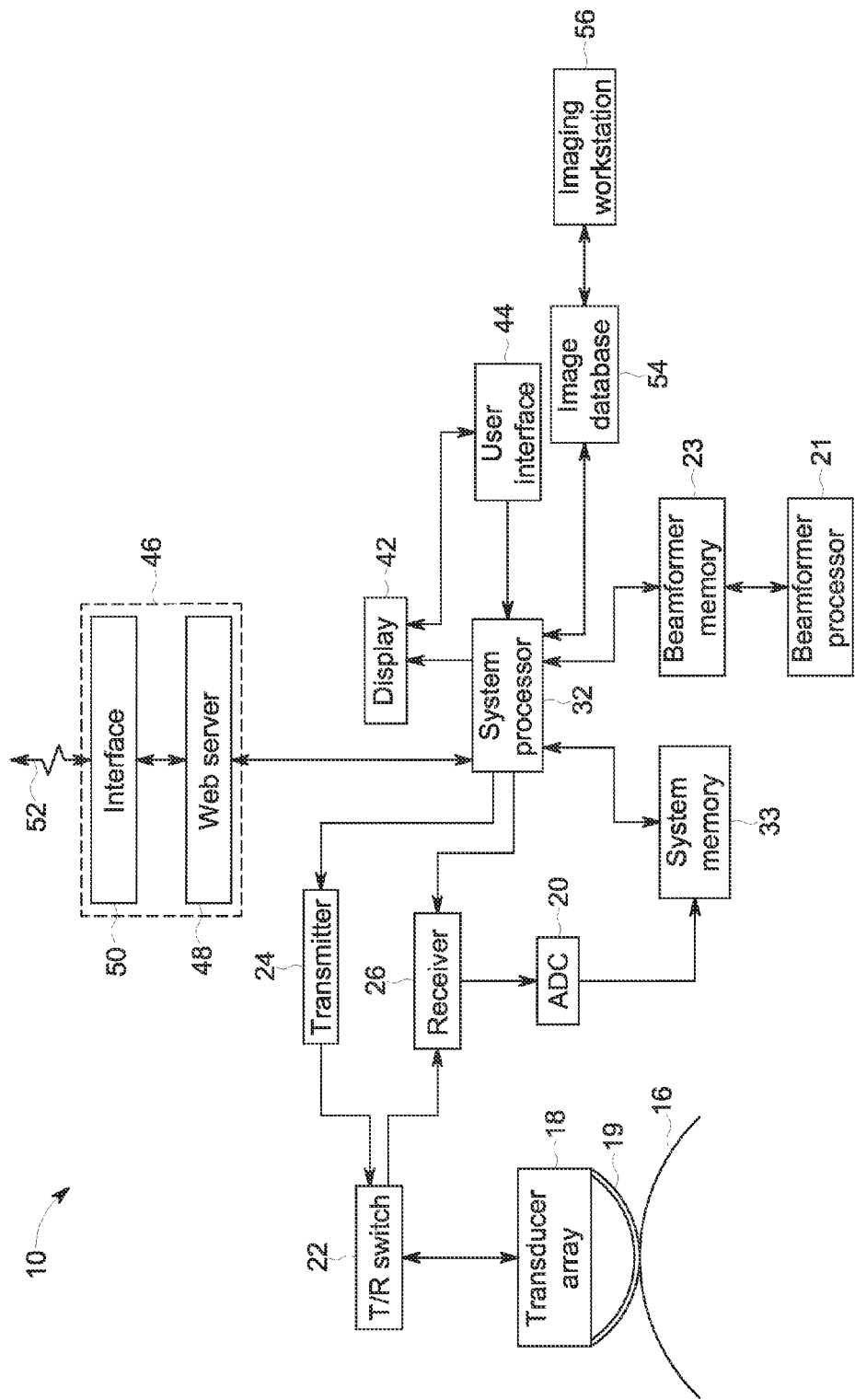
FIG. 1 is a diagrammatic view of an ultrasound system in accordance with embodiments of the present technique.

Turning now to the drawings, FIG. 1 is a diagrammatic view of an ultrasound system in accordance with embodiments of the present technique. The illustrated ultrasound system 10 includes example components connected in a manner suitable for data acquisition and processing. However, the illustrated embodiment is merely an example and is not meant to limit the forms, components, or data flow encompassed by presently disclosed embodiments. Indeed, in other embodiments, the architectures and modules of system 10 may include a variety of hardware and software components. For example, the system may include hardware components, such as circuit boards with digital signal processors. Also, the system 10 may have computer readable instructions executable on a variety of media, storage devices, or hardware, such as personal computer.

In the illustrated embodiment, a piezoelectric transducer array 18 is provided with a front face or acoustic lens structure 19 that is adapted to contact a subject 16, such that an ultrasonic scan may be performed to analyze internal features of the subject 16. Typically, the same transducer elements both generate and receive ultrasound energy in a pulse-echo mode, although different elements on the transducer may be used for these functions in some embodiments.

The transducer array 18 is connected via transmitter/receiver switching circuitry 22 to a transmitter 24 and a receiver 26. The transmitter/receiver switching circuitry 22 switches the electrical connections between the transducer array 18 and the transmitter 24 and receiver 26. In operation, the transmitter 24 is connected to the transducer array 18 when ultrasound energy has to be transmitted into the body of the subject 16, and the receiver circuitry 26 is connected to the transducer array 18 when the transducer array 18 receives the echo signals from the tissue layers of the subject 16.

That is, the illustrated transducer array 18 comprises a two-way transducer. When ultrasound waves are transmitted into a subject 16, the ultrasound waves are backscattered off the tissue and blood within the subject 16. The transducer elements of the transducer array 18 receive the backscattered waves at different times, depending on the distance into the tissue they return from, and the angle with respect to the surface of the transducer array 18 at which they return. The transducer elements are responsive to the backscattered waves and convert the ultrasound energy from the backscattered waves into electrical signals.

The electrical signals received by the transducer array 18 are routed through the transmitter/receiver switching circuitry 22 to the receiver 26. The receiver 26 amplifies the received signals after proper gain compensation, and an analog-to-digital converter (ADC) 20 converts these received analog signals from each transducer array element to digitized signals sampled uniformly in time, which are stored temporarily in system memory 33. The digitized signals correspond to the backscattered waves received by each transducer element at various times. After digitization, the signals still preserve the amplitude and phase information of the backscattered waves.

The system processor 32 retrieves the element signals from the system memory 33 and transfers them to beamformer memory 23. In some implementations, the system processor 32 may modify the element signals, such as converting them to baseband signals or compressing the signals. In other implementations, these additional processing steps may be perform in dedicated hardware before the signals are stored in the system memory 33.

A beamformer processor 21 reads the element signals from the beamformer memory 23, performs the beamforming steps as described in more detail below, produces the beamsummed signal, and writes the beamsummed signal to the beamformer memory 23. The system processor 32 reads the beamsummed signal from the beamformer memory 23 and processes the beamsummed signals from various transmit events to form an image, which may be displayed on a display 42 if desired in the given embodiment.

In the illustrated embodiment, the beamforming processing is performed in a processor (i.e., beamformer processor 21) separate from the system processor 32. However, it should be noted that in other embodiments, the beamforming processing may be performed in the system processor 32, or in any other suitable circuitry in the system 10.

In the illustrated embodiment, the system 10 also includes a user interface 44 that is in communicative coupling with the system processor 32 and the display unit 42 to enable a user to communicate with the processor 32, for example, to input one or more desired imaging or display parameters. In certain embodiments, the system processor 32 may also be coupled to a remote connectivity module 46 having a web server 48 and a remote connectivity interface 50 for coupling the ultrasound system to a network, via link 52. System processor 32 may be further coupled to an image database 54 to receive ultrasound image data. In turn, the image database 54 may be in communicative coupling with imaging workstation 56.

Figure 2:
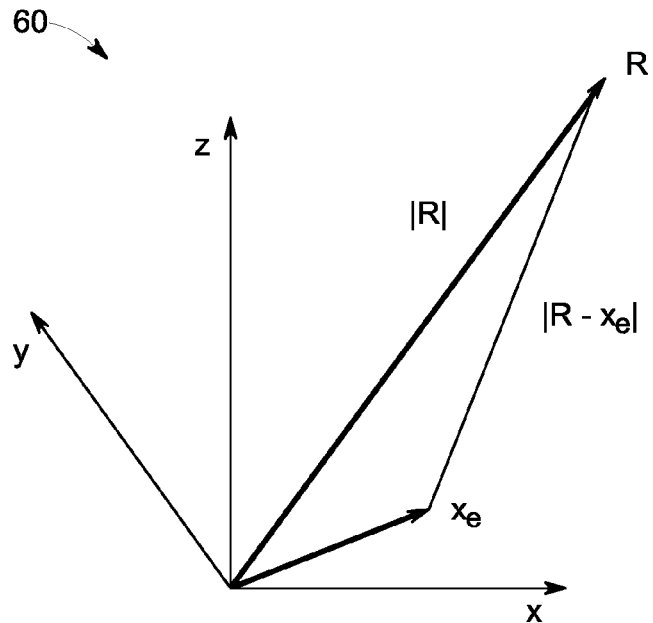
FIG. 2 is a diagrammatic view of beamforming geometry in accordance with an embodiment.

FIG. 2 is a schematic 60 illustrating the beamforming geometry. The desired beam lies along the vector R, which originates at the vector x=0. The element position is $x_e$. The equally spaced output samples correspond to a set of equally spaced ranges |R| along the beam direction, as given by the following:

$$ict_s = 2|R(i)|, \quad (1)$$

where i is the sample number, an integer value, c is the sound propagation speed, and $t_s$ is the sampling time interval; the factor of two accounts for the two-way propagation of sound from the origin to the focus point R(i) and back to the origin. For an element at $x_e$, these equally spaced output samples correspond to a set of unequally spaced sampling times (1/c)[|R(i)|+|R(i)−$x_e$|], which is the time required for sound to propagate from the origin to the focus point R(i) and back to the element at $x_e$. Since the available element samples are equally spaced in time, the desired element sample values are typically obtained by interpolation.

It should be noted that for simplicity, the beamsum is described herein as corresponding to a set of focus points which lie along a (straight) line oriented in a particular direction. However, it will be appreciated that more generally, with the proper choice of focus function, a beamformer may produce a beamsum which corresponds to a set of focus points which lie along a curve, and presently disclosed embodiments are not limited to those in which the beamsum corresponds to focus points which lie along a straight line.

The methods and techniques provided herein invert this procedure by instead mapping the equally spaced samples of a particular element signal to a set of unequally spaced output samples and performing the interpolation on the output:

$$ict_s = |R| + |R - x_e|. \quad (2)$$

Equation (2) can be solved for R≡|R|:

$$2R = \frac{(ict_s)^2 - |\vec{x}_e|^2}{ict_s - \vec{x}_e \cdot \hat{R}}. \quad (3)$$

With the definitions:

$$\beta \equiv 2R/ct_s \quad (4)$$

$$g(|x_e|) \equiv |x_e|/ct_s$$

$$h(x_e \cdot \hat{R}) \equiv x_e \cdot \hat{R}/ct_s = \hat{x}_e \cdot \hat{R} g,$$

then $$\beta(i, g, h) = \frac{i^2 - g^2}{i - h} \quad (5)$$
$$= i + h + \frac{h^2 - g^2}{i - h}$$

where β(i,g,h) is the non-integer sample number in the output corresponding to the integer sample number i in the signal for element $x_e$ and beam direction $\hat{R}$. As used herein, the term "non-integer sample number" represents a time that is not, in general, one of the uniformly spaced sampling times. The quantity g is the dimensionless distance of the element from the origin, and h is the projection of the element position vector onto the beam direction, also in dimensionless units. Note that in the foregoing analysis, it has been assumed that the element and beamsum signals are sampled at the same rate, but this assumption is used only for simplicity, and is not meant to limit presently disclosed embodiments.

The singularity in β at i=h is unphysical. From Equation (2), i c $t_s$→|$x_e$|/c $t_s$=g for R→0, so that the minimum relevant value of i is g, which is non-negative. From Equation (4), we see that when h is non-negative, it is never larger than g. Thus, the denominator in Equation (5) will never vanish in practice. More precisely, the minimum value of i is ceil(g), the smallest integer not smaller than g. The special case $x_e$=0 must also be avoided, but for this case, the desired element sampling times are just the uniformly spaced beamsum sample times.

These equations guide the presently disclosed embodiments of the inversion of the typical focusing equation for imposing beamforming time-delays. This inverted beamforming may be better understood by considering the schematics 62 and 64 in FIGS. 3 and 4 that illustrate the conventional beamforming approach and the inverted beamforming approach, respectively. More specifically, the schematic 62 of FIG. 3 includes a time axis 66, a set of uniformly spaced sample times for a beamsum signal 68, a set of uniformly spaced sample times for an element signal 70, and a focus delay 72. In the illustrated embodiment, the set of beamsum sample times 68 includes a desired output sample time 74, and the set of element signal sample times 70 includes input sample times 76 and 78 between which the focus delay line 72 is located. Further, the schematic 64 of FIG. 4 includes a time axis 80, a set of beamsum signal sample times 82, a set of element signal samples times 84, and focus delay lines 86 and 88.

Figure 3:
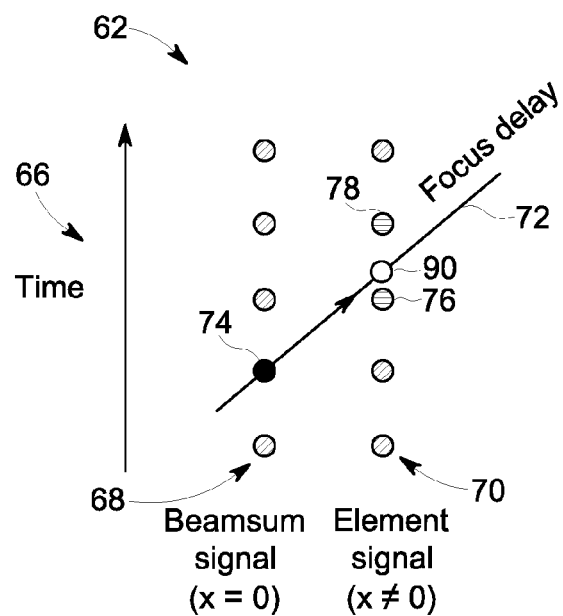
FIG. 3 is a diagrammatic view illustrating an example of a beamforming technique.

In FIG. 3., the diagonal line 72 represents the relative focus delay, with respect to the transducer array center, calculated for an element at some nonzero distance, x, from the origin of the beam for the beamsum sample time 74. In the conventional beamforming approach of FIG. 3, the focus delay 72 is calculated to give the non-integer sample time in the input signal (the element signal) corresponding to the integer sample time in the output signal (the beamsum signal). As used herein, the term "integer sample time" refers to one of the uniformly spaced sample times, that is, a sample time which is an integer multiple of a sampling time interval. Further, as used herein, the term "non-integer sample time" refers to a sample time which is not in general an integer multiple of a sampling time interval. Thus, in FIG. 3., the focus delay line 72 passes through beamsum sample 74 but passes between element samples 76 and 78 at the non-integer sample time 90. In the conventional beamforming approach, the value of the element signal at the desired sample time 90 is obtained by interpolation between the element signal samples. Such an interpolation is performed for every element signal in the transducer array 12.

Figure 4:
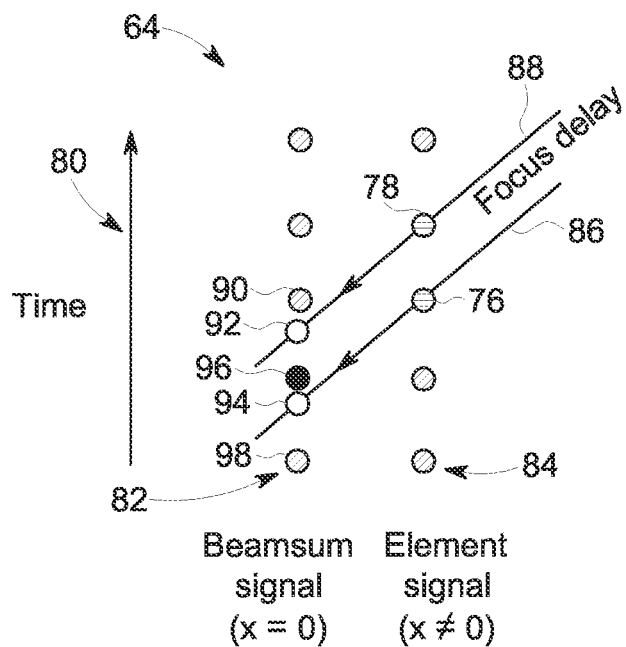
FIG. 4 is a diagrammatic view illustrating an embodiment of an inverted beamforming technique.

In the inverted beamforming approach illustrated in the schematic 64 of FIG. 4, the focus delays are instead calculated to give the non-integer sample times in the output signal (the beamsum) corresponding to the integer sample times in the input signal (the element signal). Thus, the focus delay represented by diagonal line 86 passes through element sample 76 but between the beamsum samples 98 and 96, at the non-integer sample time 94. Similarly, the focus delay represented by diagonal line 88 passes through element sample 78 but between the beamsum samples 96 and 90, at non-integer sample 92. The desired values in the beamsum, at the integer sample times, are calculated by interpolating the values at the non-integer sample times.

Figure 5:
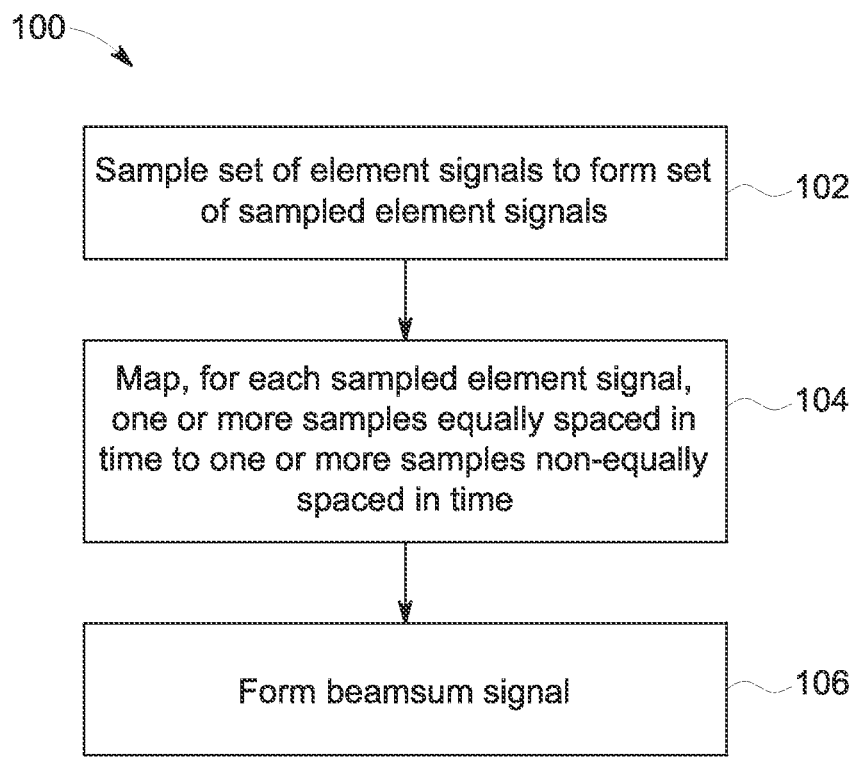
FIG. 5 is a flow diagram illustrating an embodiment of an inverted beamforming method.

An embodiment of a method 100 suitable for performing this inverted beamforming approach is shown in FIG. 5. As illustrated, the method 100 includes sampling, substantially uniformly in time, a set of continuous-time element signals to form a set of sampled element signals (block 102). Further, the method 100 calls for mapping, for each sampled element signal, one or more samples substantially equally spaced in time to one or more samples non-equally spaced in time corresponding to the respective contribution of each element signal to a continuous-time beamsum signal (block 104). The method also includes forming a beamsum signal sampled substantially uniformly in time from the non-uniformly spaced, mapped samples corresponding to each sampled element signal (block 106), for example, as described in detail above with respect to FIG. 4.

Embodiments of the presently disclosed inverted beamforming systems and methods provided herein may offer a variety of advantages over conventional beamforming approaches. For example, in conventional beamforming, whether performed in hardware or software, each element signal must be interpolated to implement the beamforming time-delay operation. However, in the presently disclosed inverted beamforming approach, the beamsum signal, not the element signals, is interpolated. In many ultrasound imagers, the number of beamsum signals calculated for a given transmit firing is much smaller than the number of element signals. Accordingly, in certain embodiments, by utilizing the disclosed inverted beamforming approach, fewer computations may be necessary, thus providing for reductions in power and monetary cost.

In addition, in conventional beamforming, the sampling frequency of the digital element signals is typically much greater than the Nyquist sampling frequency in order to reduce the cost and complexity of the interpolation hardware, or the computational power needed when the interpolation is performed in software. The Nyquist sampling frequency is the theoretical minimum sampling rate need to reconstruct a signal at any arbitrary time from its sampled values. The cost and complexity of an ADC typically increases with sampling rate, but generally, using a relatively high sampling rate minimizes the total system cost of a traditional beamformer. However, in the presently disclosed inverted beamforming approach, only the beamsum signal is interpolated, so the sampling rate of the large number of element signals may be reduced, and the complexity of the interpolating software of the small number of beamsum signals may be increased to achieve substantially the same performance as a traditional beamformer but at a lower system cost.

Figure 6:
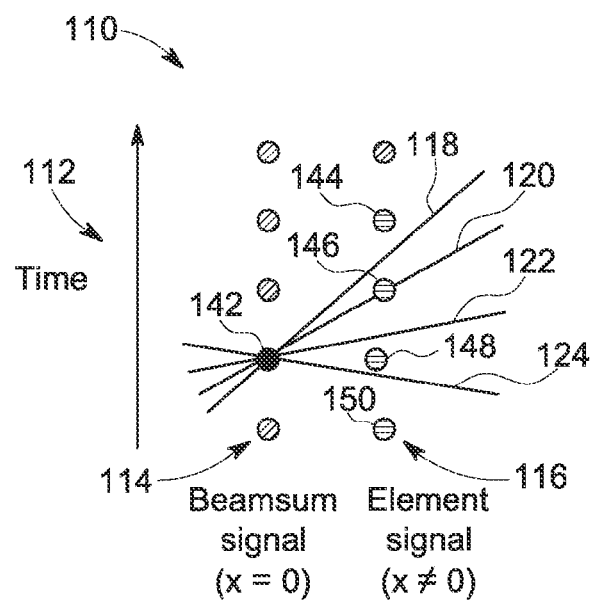
FIG. 6 is a diagrammatic view illustrating an example of sample mapping in a beamforming technique.
Figure 7:
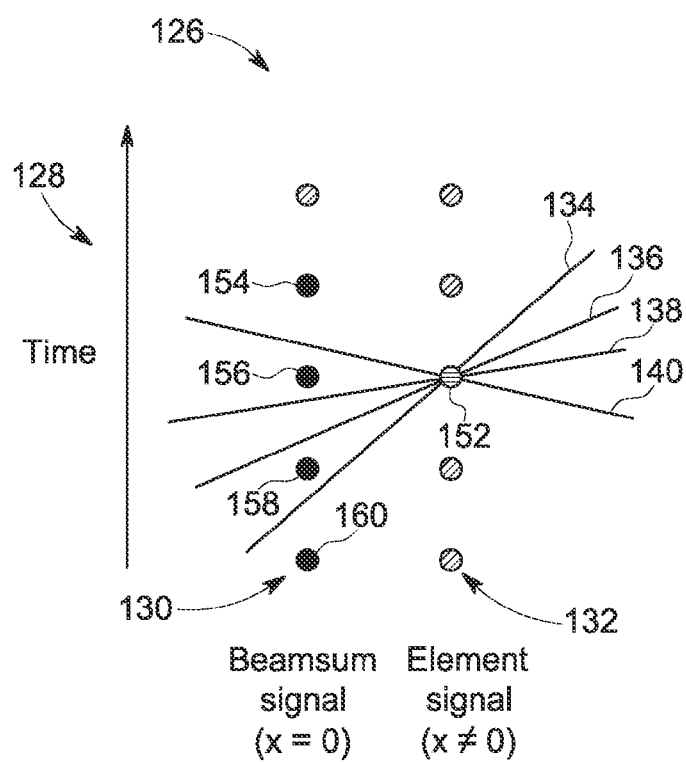
FIG. 7 is a diagrammatic view illustrating an embodiment of sample mapping in an inverted beamforming technique.

FIGS. 6 and 7 illustrate an advantage associated with the presently disclosed inverted beamforming approach when the beamforming is performed in software. More specifically, the foregoing figures illustrate that when implementing beamforming in software utilizing the presently disclosed inverted beamforming may enable more efficient memory access patterns when compared to implementing conventional beamforming in software. In particular, FIG. 6 illustrates a schematic 110 corresponding to a conventional beamforming approach and having a time axis 112, a set of beamsum signal samples 114, a set of element signal samples 116, and lines 118, 120, 122, and 124 representing the focus delay functions for a conventional beamformer for a set of beamsum signals steered in different directions. FIG. 7 illustrates a schematic 126 corresponding to an inverted beamforming approach and having a time axis 128, a set of beamsum signal samples 130, a set of element signal samples 132, and lines 134, 136, 138, and 140 representing the focus delay functions for an inverted beamformer for a set of beamsum signals steered in different directions. It should be noted that in the conventional beamformer, as represented in FIG. 6, the focus delay lines 118, 120, 122 and 124 all pass through a beamsum sample 142, while in the inverted beamformer, FIG. 7, the focus delay lines 134, 136, 138 and 140, all pass through an element sample 152.

The implementation of a conventional software beamformer, as depicted in FIG. 6, typically loops over the output beamsum samples, mapping each output sample using the focus function for each beamsum to a neighborhood of input samples for each transducer element. The memory access for the beamsum signals is sequential as the beamformer calculations proceed from one output sample to the next, but the memory access to the element samples is not. As an example, for linear interpolation, a pair of bracketing element samples is required, and this pair will generally be different for each desired beamsum signal. In other words, each output sample, for example, sample 142, in general maps to different bracketing input samples, for example, samples 144, 146, 148, and 150, for the different beamsums corresponding to focus delays 118, 120, 122, and 124.

However, in the inverted beamforming approach illustrated in the schematic 126 of FIG. 7, the calculation loop is over the element samples, so that memory access to the element samples is sequential regardless of how many beamsums are calculated, while memory access to the output samples is not sequential. Accordingly, in some embodiments in which there are many more elements than beamsums, the memory access pattern for the inverted beamforming approach may present one or more desired advantages. Furthermore, whereas the conventional approach (with linear interpolation) requires two element memory accesses for each output beamsum sample, in certain embodiments, the inverted beamformer can be implemented so that it requires only one element memory access for each output beamsum sample for the vast majority of output samples (those in which only a single integer sample lies between adjacent non-integer samples, i.e., those cases in which only one integer lies between $\beta(i)$ and $\beta(i+1)$).

As described in detail above, the inverted beamforming approach produces, as an intermediate step, non-uniformly spaced contributions to the beamsum from each element signal. Typically, however, it is more convenient to have uniformly spaced beamsum samples for subsequent processing steps such as filtering and scan conversion. The techniques discussed above describe one method (i.e., interpolation) for converting the non-uniformly spaced samples to uniformly spaced samples. However, it should be noted that presently disclosed embodiments are not limited to the use of interpolation. Indeed, any of a variety of suitable methods for converting the non-uniformly spaced samples to uniformly spaced samples may be utilized. For example, in one embodiment described in more detail below, an oversampling method may be used instead of interpolation. However, again, any suitable method may be utilized in other embodiments.

In general, in one suitable oversampling embodiment, an output buffer for a beamsum signal with an increased or high sampling rate with respect to the input signal sampling rate is provided. In one embodiment, the sampling rate may be approximately twenty times the sampling rate that would normally be used for the element and beamsum signals. For example, when imaging with a center frequency of 5 MHz, a sampling rate of 50 MHz might traditionally be used for the element and beamsum signals, so the output buffer would use a sampling rate of 1 GHz. In one embodiment, the output buffer is initialized to zero and then each non-uniformly spaced element sample is added to the value in the buffer at the nearest position corresponding to the value $\beta$ taking into account the higher sampling rate in the beamsum compared with the element signal. For example, if the oversampling factor p is twenty, then the sample would be added to the value in position Round (p $\beta$), where the Round( ) operation returns the nearest integer to its argument. Once all the time-delayed samples for all the elements for a given beam direction are added to the output buffer, the buffer is lowpass filtered and decimated to the desired output sampling rate.

Figure 8:
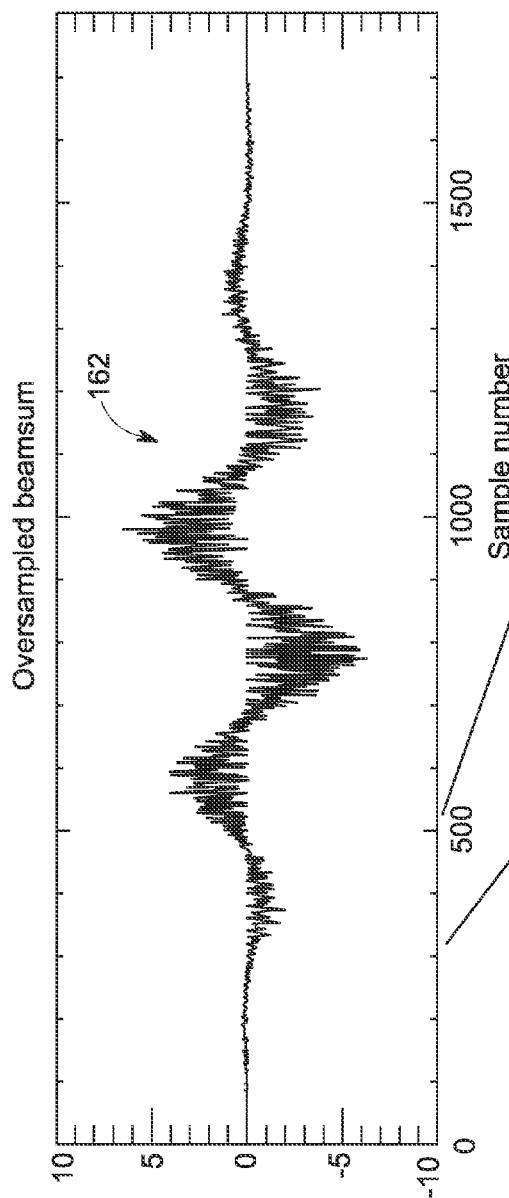
FIG. 8 is a graph illustrating representative values in an output buffer in accordance with an embodiment.
Figure 9:
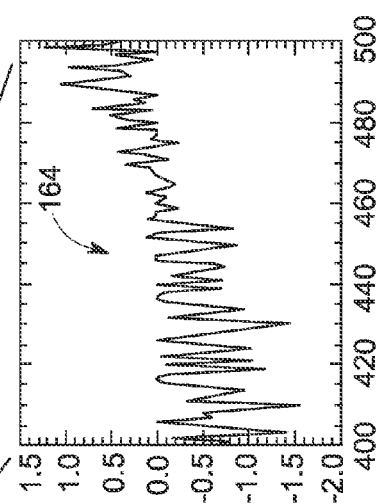
FIG. 9 illustrates a portion of the graph of FIG. 8 in more detail.
Figure 10:
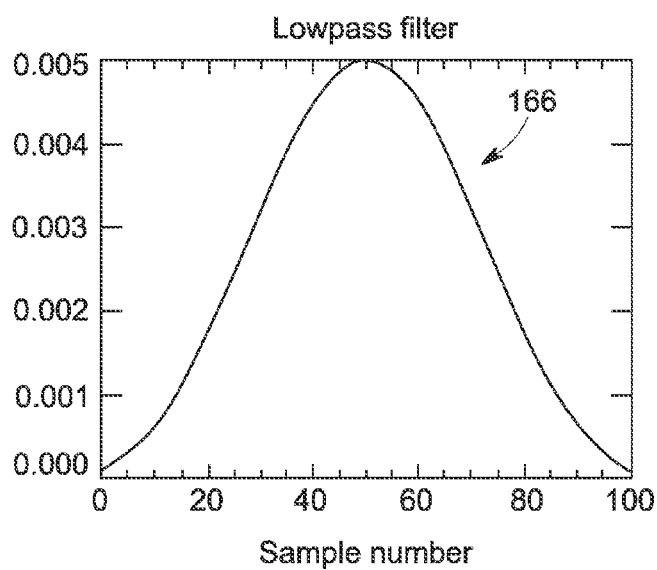
FIG. 10 is a graph illustrating an embodiment of the values in a digital low pass filter that may be utilized to filter the values stored in the output buffer of FIG. 8.
Figure 11:
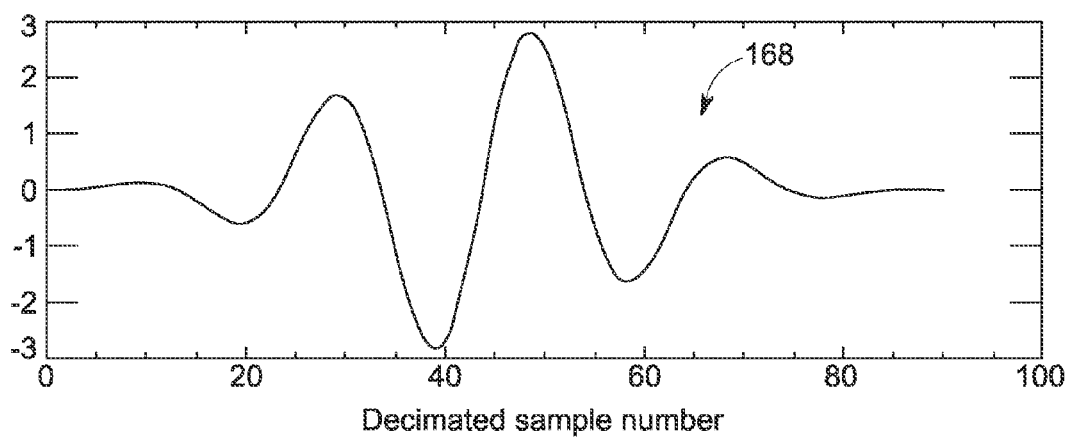
FIG. 11 is a graph illustrating the representative values of an oversampled beamsum signal stored in the output buffer of FIG. 8 after modification by low pass filtering and decimation in accordance with an embodiment.

FIGS. 8-11 illustrate these steps in more detail. Specifically, FIG. 8 illustrates a portion of the contents of an output buffer 162 for a simulated receive beam steered toward point-like scatterer after all the time-delayed element samples have been added. FIG. 9 illustrates a portion 164 of the graph 162 shown in FIG. 8. As shown, the amplitude of the oversampled signal varies considerably around its local mean value. FIG. 10 illustrates a lowpass filter 166, an approximately Gaussian envelope with a width of about the length of the receive impulse response. Further, FIG. 11 illustrates a smoothed signal 168, which is the result of lowpass filtering and decimating the oversampled beamsum signal. In the simulated embodiment, the smoothed signal result closely approximates the ideal beamformed signal from a point-like target.

In some embodiments, by utilizing the oversampling method shown in FIGS. 8-11 instead of linear interpolation, the inaccuracies inherent in linear interpolation may be avoided. Further, in certain embodiments, utilizing the oversampling method may be computationally more efficient when the number of elements exceeds a predetermined threshold since the only operation applied to the element samples is Round( ) in contrast to linear interpolation, where a weighted sum of two neighboring samples must be calculated. Further, the necessary low pass filtering is applied only to the beamsum signal, which typically has far few samples than does the set of element signals, so that the computational complexity is reduced. However, it should be noted that the method chosen for converting the non-uniformly spaced samples to uniformly spaced samples in a given implementation may vary in different embodiments, depending on implementation-specific considerations. Indeed, any desired method for converting the non-uniformly spaced samples to uniformly spaced samples may be utilized, not limited to those disclosed herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A beamforming method, for use in an ultrasound system, comprising:
    sampling using a beamformer processor of the ultrasound system, uniformly in time, a set of continuous-time element signals to form a set of sampled element signals;
    mapping using the beamformer processor of the ultrasound system, for each sampled element signal, samples of element signals equally spaced in time to output samples non-equally spaced in time corresponding to the respective contribution of each sampled element signal to a continuous-time beamsum signal to generate non-equally spaced, mapped samples based on beam direction and element position;
    forming using the beamformer processor of the ultrasound system, a beamsum signal sampled uniformly in time from the non-equally spaced, mapped samples corresponding to each sampled element signal; and
    generating an image based on the beamsum signal.

2. The method of claim 1, wherein forming the beamsum signal comprises interpolating the non-equally spaced, mapped samples.

3. The method of claim 2, wherein forming the beamsum signal from non-equally spaced, mapped samples comprises linearly interpolating samples between one or more pairs of non-equally spaced, mapped samples.

4. The method of claim 1, wherein forming the beamsum signal comprises oversampling the beamsum signal compared to the sampled element signal, assigning each of the non-equally spaced, mapped samples to a nearest over-sampled position and reducing a sampling rate of the over-sampled beamsum signal to a desired sampling rate.

5. An ultrasound system, comprising:
    a transducer array comprising one or more transducers;
    a transmitter configured to transmit electrical signals to the transducer array;
    a receiver configured to receive electrical signals generated by the transducer array when the one or more transducers detect an ultrasonic echo;
    transmitter/receiver switching circuitry coupled to the transducer array and configured to switch the transmitter and the receiver;
    an analog-to-digital converter configured to receive analog data from the receiver corresponding to the ultrasonic echo and to convert the analog data to a digital element signal; and
    a beamformer processor configured to receive and process the digital element signal to form a beamsum signal, wherein the beamformer processor is configured to sample, uniformly in time, a set of continuous-time element signals to form a set of sampled element signals, to map, for each sampled element signal, samples of element signals equally spaced in time to output samples non-equally spaced in time corresponding to the respective contribution of each sampled element signal to a continuous-time beamsum signal to generate non-equally spaced, mapped samples based on beam direction and element position, to form the beamsum signal sampled uniformly in time from the non-equally spaced, mapped samples corresponding to each sampled element signal, and to generate an image based on the beamsum signal.

6. The system of claim 5, wherein the beamformer processor is configured to form the beamsum signal by interpolating the non-equally spaced, mapped samples.

7. The system of claim 6, wherein the beamformer processor is configured to form the beamsum signal from the non-equally spaced, mapped samples by linearly interpolating samples between one or more pairs of the non-equally spaced, mapped samples.

8. The system of claim 5, comprising a system processor, wherein the system processor is configured to receive the beamsum signal from a beamformer memory and to process beam summed signals from a variety of transmit events to form image data corresponding to the image.

9. The system of claim 8, comprising a scan converter configured to receive the image data and to convert the image data to geometrically corrected pixel data.

10. The system of claim 9, comprising a display processor configured to receive the digital pixel data from the scan converter and to filter and convert the digital pixel data to produce analog data.

11. The system of claim 10, further comprising a display, wherein the display processor is configured to display at least one of the analog data corresponding to the digital pixel data and the image on the display.

12. The system of claim 11, comprising a user interface configured to receive one or more user inputs that enable the user to control one or more parameters of the image displayed on the display.

13. The system of claim 5, comprising a remote connectivity module having a webserver and a remote connectivity interface, coupled to a system processor and configured to couple the system to an external network.

14. The system of claim 5, further comprising an imaging workstation coupled to an imaging database configured to store data corresponding to the ultrasound echo.

15. The system of claim 5, comprising an image database coupled to a system processor and configured to enable transfer of ultrasonic image data from the image database to memory associated with the beamformer processor.

16. A non-transitory computer readable medium encoding one or more executable routines, which, when executed by a processor, cause the processor to perform acts of a beamformer method for use in an ultrasound system, comprising:
sampling using a beamformer processor of the ultrasound system, uniformly in time, a set of continuous-time element signals to form a set of sampled element signals;
mapping using the beamformer processor of the ultrasound system, for each sampled element signal, samples of element signals equally spaced in time to output samples non-equally spaced in time corresponding to the respective contribution of each sampled element signal to a continuous-time beamsum signal to generate non-equally spaced, mapped samples based on beam direction and element position;
forming using the beamformer processor of the ultrasound system, a beamsum signal sampled uniformly in time from the non-equally spaced, mapped samples corresponding to each sampled element signal; and
generating an image based on the beamsum signal.

17. The non-transitory computer readable medium of claim 16, wherein forming the beamsum signal comprises interpolating the non-equally spaced, mapped samples.

18. The non-transitory computer readable medium of claim 17, wherein forming the beamsum signal from non-equally spaced, mapped samples comprises linearly interpolating samples between one or more pairs of non-equally spaced, mapped samples.

19. The non-transitory computer readable medium of claim 16, wherein forming the beamsum signal comprises oversampling the beamsum signal compared to the sampled element signal, assigning each of the non-equally spaced, mapped samples to a nearest oversampled position and reducing a sampling rate of the oversampled beamsum signal to a desired sampling rate.

20. The non-transitory computer readable medium of claim 16, wherein the processor is further configured to process beam summed signals from a variety of transmit events to form image data corresponding to the image.

* * * * *